United States Patent [19]

Steer et al.

[11] 4,341,207
[45] Jul. 27, 1982

[54] WOUND DRESSING

[75] Inventors: Peter L. Steer, East Grinstead; Howard Mathews, Forest Row, both of England

[73] Assignee: Kingsdown Medical Consultants Limited, England

[21] Appl. No.: 180,717

[22] Filed: Aug. 25, 1980

[30] Foreign Application Priority Data

Sep. 7, 1979 [GB] United Kingdom ............... 7931164
Apr. 21, 1980 [GB] United Kingdom ............... 8012994

[51] Int. Cl.³ .................................... A61F 13/00
[52] U.S. Cl. ...................................... 128/155; 128/156
[58] Field of Search ....................... 128/155, 156, 283; 428/354

[56] References Cited

U.S. PATENT DOCUMENTS

| 2,465,357 | 3/1949 | Correll | 106/122 |
| 2,558,395 | 6/1951 | Studer | 167/65 |
| 3,029,187 | 4/1962 | Steinhardt | 167/60 |
| 3,121,021 | 2/1964 | Copeland | 128/156 |
| 3,339,546 | 9/1967 | Chen | 128/156 |
| 3,416,525 | 12/1968 | Yeremian | 128/156 |
| 3,645,845 | 2/1972 | Hodgson | 128/156 |
| 3,709,221 | 1/1973 | Riely | 128/156 |
| 3,767,784 | 10/1973 | Gluck | 424/28 |
| 3,972,328 | 8/1976 | Chen | 128/156 |
| 4,120,175 | 10/1978 | Ockwell et al. | 128/283 |
| 4,192,785 | 3/1980 | Chen et al. | 260/17.4 |
| 4,292,972 | 10/1981 | Pawelchak et al. | 128/296 |

FOREIGN PATENT DOCUMENTS

| 386067 | 1/1933 | United Kingdom . |
| 548046 | 9/1942 | United Kingdom . |
| 723431 | 2/1955 | United Kingdom . |
| 732164 | 6/1955 | United Kingdom . |
| 768677 | 2/1957 | United Kingdom . |
| 1301101 | 12/1972 | United Kingdom . |
| 1313134 | 4/1973 | United Kingdom . |
| 1351439 | 5/1974 | United Kingdom . |
| 2023430 | 1/1980 | United Kingdom . |

OTHER PUBLICATIONS

"Better Decubitus Care", Nursing 76, Apr., p. 13.
"Flexible Decubitus Treatment", Nursing Care, 7/76, p. 24, Baum.
"The Enterocutaneous Fistula", Nursing 78, Apr. 78, Geels et al.
"Pressure Sores", Nursing 79, Jan. 79, Cameron.
"The Use of Stomadhesive in the Care of the Skin", Surgery, Gyn. & Obs., 9/76, pp. 449–451, vol. 143.

Primary Examiner—Kyle L. Howell
Assistant Examiner—T. J. Wallen
Attorney, Agent, or Firm—Lawrence S. Levinson; Stephen B. Davis

[57] ABSTRACT

A multi-layered dressing including a layer of curative and absorbant material which contacts the wound, an intermediate layer of deodorizing material, and an air and gas permeable outer flexible layer which secures the dressing to the body.

16 Claims, 6 Drawing Figures

WOUND DRESSING

BACKGROUND OF THE INVENTION

Chen in U.S. Pat. No. 3,339,546 describes adhesive compositions for adhering to moist body surface. The compositions include one or more water soluble or swellable hydrocolloids and viscous binding substance such as polyisobutylene. The adhesive composition can have a layer of polymeric film secured to one surface. Among the compositions disclosed by Chen is a blend of the hydrocolloids pectin, gelatin and sodium carboxymethylcellulose and polyisobutylene to which a polyethylene film is secured. This composition is available commercially under the trademark Stomahesive.

The use of Stomahesive in the care of decubitus ulcers and pressure sores has been described in the nursing literature. In general, these treatments involve employing Stomahesive to protect the skin around the wound or as an outer wrap over the open wound as note Leeson, "Better Decubitus Care" in Nursing 76, April 1976, p. 13, Baum, "Flexible Decubitus Treatment" in Nursing Care, July 1976, p. 24-25, Geels et al., "The Enterocutaneous Fistula: Supplanting Surgery with Meticulous Nursing Care", Nursing 78, April 1978, and Cameron, "Pressure Sores: What To Do When Prevention Fails", Nursing 79, January, 1979, p. 42-47.

Chen in U.S. Pat. No. 3,972,328 discloses a multi-layered dressing consisting of a semi-open cell flexible polymeric foam having a water impervious polymeric film backing on one side and a hydrocolloid containing pressure sensitive adhesive on the other.

Chen et al. in U.S. Pat. No. 4,192,785 disclose an adhesive composition including hydrocolloid gums, a viscous elastic binder, and a cohesive strengthening agent.

SUMMARY OF THE INVENTION

This invention is directed to a multi-layered bandage useful in the treatment of open wounds such as decubitis ulcers. A problem with treating certain wounds, particularly ulcerated sores, is to meet the conflicting requirements of providing a comfortable covering which protects the wound and substantially deodorizes any escaping gas without impeding the passage of such gas away from the wound area.

The multi-layered bandage of this invention includes at least a layer of curative and absorbent material which contacts the wound, a layer of deodorizing material, and an outer flexible layer that secures the bandage to the body.

DETAILED DESCRIPTION OF THE INVENTION

This invention is directed to a multi-layered bandage or dressing. The dressing includes a layer of curative and absorbent material which contacts the wound, a layer of deodorizing material, and an outer flexible layer that secures the bandage to the body.

Figure 1:
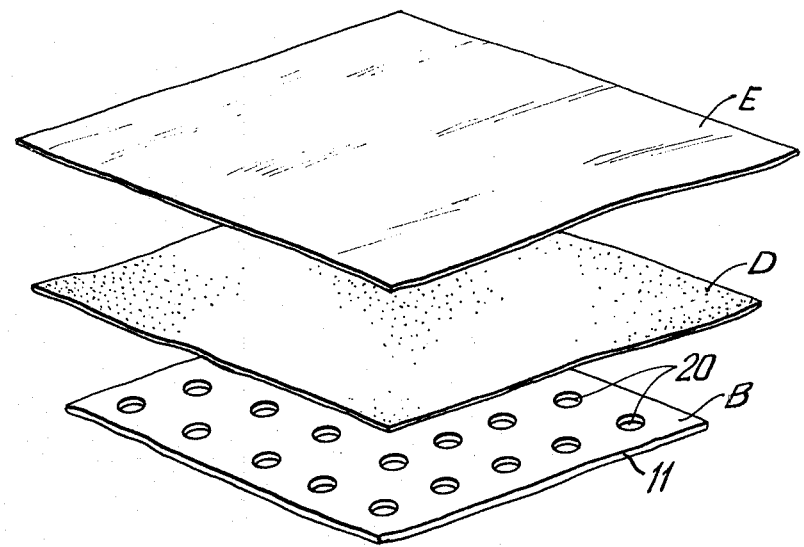
FIG. 1 is an exploded view of a multi-layered bandage of this invention.
Figure 2:
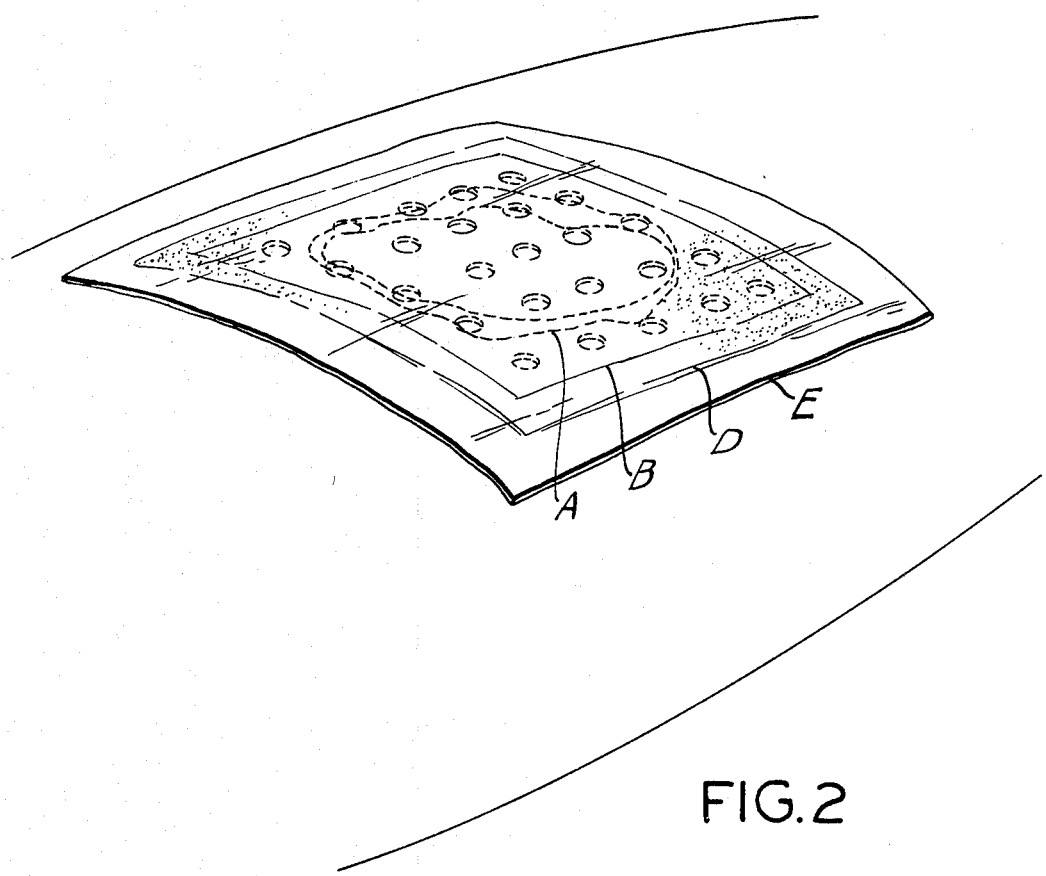
FIG. 2 is a perspective view of the bandage of FIG. 1 applied to a wound.
Figure 4:
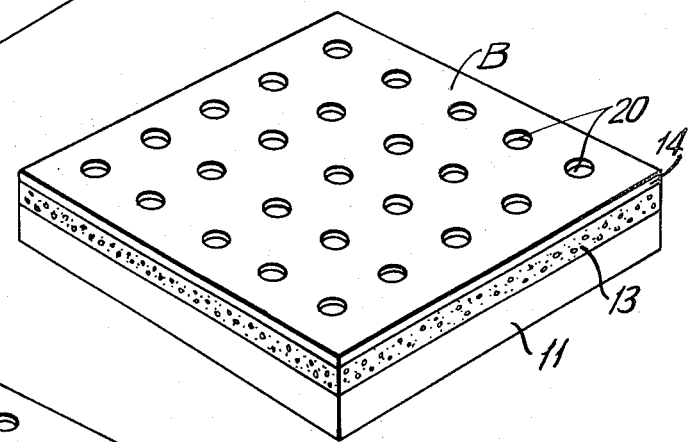
FIG. 4 is an enlarged view of another alternate layer B.
Figure 5:
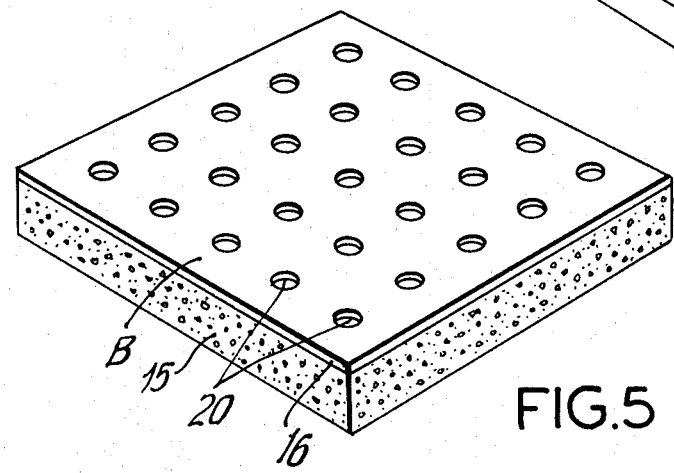
FIG. 5 is an enlarged view of still another alternate layer B.

The layer of curative and absorbent material is shown in the Figures as layer B. Layer B may be formed entirely as a homogeneous cohesive mass 11 as shown in FIGS. 1 and 2, layer B may be formed as a homogeneous cohesive mass 11 having a backing film 12 as shown in FIG. 3, layer B may be formed as homogeneous mass 11 having as the backing an intermediate layer of semi-open cell polymeric foam 13 and an optional outer polymeric film 14 as shown in FIG. 4, or layer B may be formed as a curative and absorbent foam 15 which may have an optional backing film 16 as shown in FIG. 5.

The layer B has a plurality of apertures 20 extending through the curative and absorbent homogeneous mass or foam material and any of the optional backings that may be present. The apertures may be in a regular pattern or randomly placed. The ratio between the surface area of layer B and the apertures can vary from about 1:2 to 2:1, with about 1:1 being preferred. The apertures can be punched through layer B or may be formed by a molding operation. The particular shape and dimensions of layer B are not critical. The rectangular shape shown in the drawings is preferred though it may be desirable in treating wounds at various body locations such as the elbow or heel to have a circular shape. The layer B may vary in thickness from about 1 to about 4 mm. and the apertures may have a diameter of from about 2 to about 4 mm.

The homogeneous cohesive mass 11 comprises a blend of one or more water soluble or swellable hydrocolloids and a natural or synthetic viscous substance which acts as a binder for the hydrocolloids. The hydrocolloids are present at from about 30% to about 70% by weight of the mass. Suitable hydrocolloids include pectin, gelatin, karaya gum, guar gum, locust bean gum, and sodium carboxymethylcellulose provided that at least about 20% by weight of the mass is one or more curative hydrocolloid substances such as pectin, gelatin and karaya gum. Suitable viscous substances include natural rubber, silicon rubber, acrylonitrile rubber, polyurethane rubber, and polyisobutylenes and such binder is also present at from about 30% to about 70% by weight of the cohesive mass. Other substances such as a plasticizer, antioxidant, or a pharmaceutically active substance such as an antibacterial agent can be included within the mass at up to about 5% by weight and a cohesive strengthening agent, for example, fibrous cotton, finely divided wood cellulose or microcrystalline cellulose can be included within the mass at up to about 10% by weight. Preferably, the homogeneous cohesive mass 11 comprises about 20% by weight of pectin, about 20% by weight of gelatin, about 20% by weight of sodium carboxymethylcellulose, and about 40% by weight of polyisobutylene.

Figure 3:
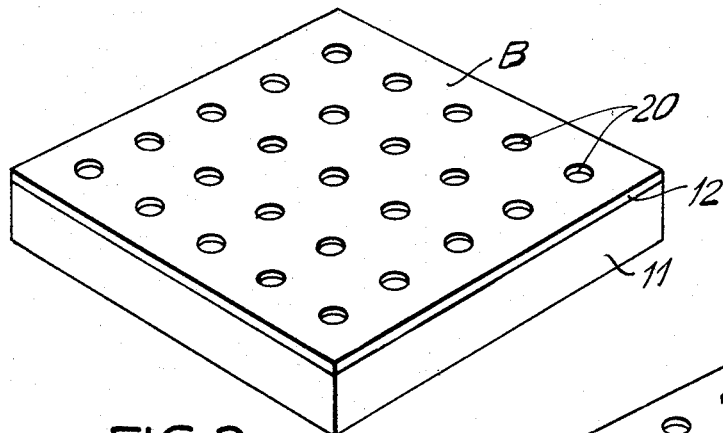
FIG. 3 is an enlarged view of an alternate layer B.

The backing film 12 as shown in FIG. 3 is secured to the surface of the homogeneous cohesive mass 11 which does not contact the wound. The film 12 is a thin sheet of polymeric material such as polyethylene, polypropylene, polyvinylchloride, etc.

As shown in FIG. 4, the cohesive mass 11 may have a layer of semi-open cell polymeric foam 13 secured to the surface which does not contact the wound. This foam can be prepared from various elastomer materials such as polyester or polyether polyurethane foams, styrene-butadiene foams, or certain rubber-based foams. The preferred material is a flexible polyurethane foam having from about 50 to about 100 cells per linear inch. By semi-open cell it is meant that the percentage of open or ruptured cells is from about 30 to about 70%. An outer polymeric film 14 from a pliable elastomer material such as flexible polyurethane, polyacrylate, polyethylene, etc., may be secured to the foam. Alternatively, instead of film 14, the top surface of foam 13 can be sealed by flaming or scorching.

The curative and absorbent homogeneous cohesive mass 11 may be prepared as taught by Chen in U.S. Pat. Nos. 3,339,546 and 3,972,328 or Chen et al. in U.S. Pat. No. 4,192,785. For example, the hydrocolloids and any optional ingredients, preferably in finely divided form, are blended and the mixture is slowly added to the viscous substance in a kneader mixer until a homogeneous mass is formed. The backing film 12 or the semi-open cell foam 13 and film 14 may then be secured and the apertures 20 punched there through. Alternatively, the homogeneous mixture of hydrocolloids and binder before setting may be molded to form the apertures 20.

The layer B of curative and absorbent material may also be a foam 15 as shown in FIG. 5. This foam can be prepared by hot air drying or lyophilizing a foamed aqueous colloidal dispersion of or more hydrocolloids such as pectin, gelatin, karaya gum, guar gum, locust bean gum, and sodium carboxymethylcellulose provided that at least about 20% by weight of the hydrocolloid dispersion is one or more curative hydrocolloid substances such as pectin, gelatin and karaya gum. Such foams are described in various patents such as U.S. Pat. Nos. 2,465,357, 2,558,395 and 3,767,784. Preferably the foam is prepared from a mixture of gelatin, pectin and sodium carboxymethylcellulose as disclosed by Pawelchak et al. in United States Application Ser. No. 167,257 filed July 9, 1980, now U.S. Pat. No. 4,292,972. This preferred foam contains from about 10% to about 50% by weight of pectin and sodium carboxymethylcellulose and from about 20% to about 80% by weight of gelatin and is prepared by dry blending the hydrocolloids, adding the blend to water with agitation so as to form a colloidal dispersion having a solids content of from about 1% to about 20% by weight, foaming the colloidal dispersion so that its volume increases from about 10% to about 60%, freezing and then freeze drying.

An optional film backing 16 of various polymeric materials such as polyethylene, polypropylene, polyvinylchloride, etc., can be secured to the surface of foam 15 which does not contact the wound.

Figure 6:
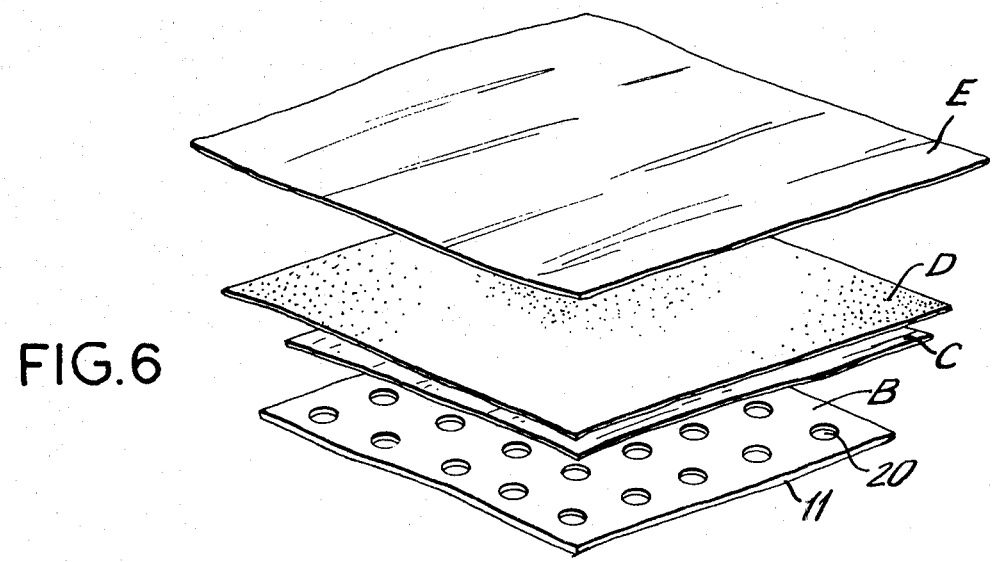
FIG. 6 is an exploded view of another embodiment of the multi-layered bandage of this invention.

The layer of deodorizing material is shown as layer D in FIGS. 1, 2 and 6. This deodorizing layer is formed of an air-permeable woven or non-woven material carrying or impregnated with a deodorizing substance. One type of suitable material is a sheet of foamed non-woven synthetic polymeric material, for example, polyurethane, having a large number of activated carbon particles distributed over one of its major surfaces. Preferably, the carbon particles are bound to the top surface, i.e., that furthest away from layer B, and the surface which contacts layer B is coated with a layer adhesive. Such a material is commercially available under the tradename Bondina. Another type of suitable deodorizing material is a layer of carbon cloth such as that disclosed by Bailey et al. in British Pat. No. 1,301,101.

As shown in FIG. 6, an intervening layer C may be included within the dressing between deodorizing layer D and curative and absorbent layer B. This intervening layer C is an air-permeable but liquid-impermeable material such as a non-woven fabric and it serves to prevent any liquid discharge which passes through layer B from escaping further. However, any gaseous discharge from the wound passes through layer C to layer D where it is deodorized. Layer C can be coated with a microporous pressure sensitive adhesive on one or both sides.

The outer layer of the wound dressing is shown as layer E in FIGS. 1, 2 and 6. This layer is a flexible breathable adhesive tape which allows air and gas to pass therethrough. This layer comprises a porous non-woven fibrous or polymeric backing having a coating of a microporous pressure sensitive adhesive on its bottom surface. Layer E extends in size beyond the periphery of layers B, D and C so that it holds the dressing together. During shipping a piece of silicon release paper is attached across the bottom of layer B and the extending portion of layer E. Examples of suitable materials for layer E are disclosed by Copeland in U.S. Pat. No. 3,121,021 and Hodgson in U.S. Pat. No. 3,645,835. It is also possible to replace the adhesive coating taught by Copeland with a hydrocolloid containing pressure sensitive adhesive such as that taught by Chen in the above noted patents. The layer E allows any gas which has been deodorized by layer D to pass to the atmosphere. Layer E also secures the dressing to the patient and provides overall protection of the wound.

The dressing of this invention is employed by placing the proper sized piece over the wound so that layer B contacts the wound. Optionally, the wound can be packed under the dressing with the hydrocolloid containing adhesive mass disclosed by Chen in U.S. Pat. No. 3,339,546, the hydrocolloid powder disclosed by Steinhardt in U.S. Pat. No. 3,029,187, karaya gum, or other healing material. This packing is represented as A in FIG. 2. The dressing is changed on a periodic bases and the wound is kept covered until the healing is complete.

What is claimed is:

1. A wound dressing comprising a layer of curative and absorbent material which contacts the wound and has a series of apertures therethrough, a layer of air-permeable deodorizing material, and and outer flexible air-permeable layer having an adhesive coating which secures the dressing to the body wherein said layer of curative and absorbent material is a homogeneous mass of from about 30% to about 70% by weight of one or more hydrocolloids selected from the group consisting of pectin, gelatin, karaya gum, guar gum, locust bean gum, and sodium carboxymethylcellulose provided that at least about 20% by weight of said mass is one or more curative hydrocolloids selected from the group consisting of gelatin, pectin and karaya gum and from about 30% to about 70% by weight of a viscous binder selected from the group consisting of natural rubber, silicone rubber, acrylonitrile rubber, polyurethane rubber and polyisobutylenes.

2. The dressing of claim 1 wherein said homogeneous mass has a thin flexible polymeric film attached to the surface which does not contact the wound and said apertures extend through said homogeneous mass and said film.

3. The dressing of claim 1 wherein said homogeneous mass has a layer of semi-open cell polymeric foam secured to the surface which does not contact the wound and said apertures extend through said homogeneous mass and said polymeric foam.

4. The dressing of claim 3 wherein said semi-open cell foam has a thin polymeric film secured to its top surface and said apertures extend through said homogeneous mass, said polymeric foam, and said film.

5. The dressing of claim 1 wherein said homogeneous mass is about 20% by weight of gelatin, about 20% by weight of pectin, about 20% by weight of sodium carboxymethylcellulose, and about 40% by weight of polyisobutylene.

6. The dressing of claim 1 wherein a layer of air-permeable liquid-impermeable non-woven fabric is included within the dressing between said curative and absorbent layer and said layer of deodorizing material.

7. The dressing of claim 1 wherein said layer of deodorizing material is a foamed non-woven synthetic material having a large number of activated carbon particles distributed over one of its major surfaces.

8. The dressing of claim 1 wherein said layer of deodorizing material is carbon cloth.

9. The dressing of claim 1 wherein said outer layer is a porous non-woven fibrous backing having a coating of microporous pressure sensitive adhesive.

10. A wound dressing comprising a layer of curative and absorbent material which contacts the wound and has a series of apertures therethrough, a layer of air-permeable deodorizing material, and an outer flexible air-permeable layer having an adhesive coating which secures the dressing to the body wherein said layer of curative and absorbent material is a foam of one or more hydrocolloids selected from the group consisting of pectin, gelatin, karaya gum, locust bean gum, guar gum and sodium carboxymethylcellulose provided that the foam contains at least about 20% by weight of one or more curative hydrocolloids selected from the group consisting of gelatin, pectin and karaya gum.

11. The dressing of claim 1 wherein said foam contains from about 10% to about 50% by weight of pectin, from about 10% to about 50% by weight of sodium carboxymethylcellulose, and from about 20% to about 80% by weight of gelatin.

12. The dressing of claim 1 wherein a thin polymeric film is secured to said foam and said apertures extend through said foam and film.

13. The dressing of claim 10 wherein a layer of air-permeable liquid-impermeable non-woven fabric is included within the dressing between said curative and absorbent foam layer and said layer of deodorizing material.

14. The dressing of claim 10 wherein said layer of deodorizing material is a foamed non-woven synthetic material having a large number of activated carbon particles distributed over one of its major surfaces.

15. The dressing of claim 10 wherein said layer of deodorizing material is carbon cloth.

16. The dressing of claim 10 wherein said outer layer is a porous non-woven fibrous backing having a coating of microporous pressure sensitive adhesive.

* * * * *